(12) United States Patent  
Imura

(10) Patent No.: US 8,130,371 B2
(45) Date of Patent: Mar. 6, 2012

(54) METHOD OF CALIBRATING REFLECTION CHARACTERISTIC MEASURING APPARATUS FOR SHEET SPECIMEN

(75) Inventor: Kenji Imura, Osaka (JP)

(73) Assignee: Konica Minolta Sensing, Inc., Osaka (JP)

( * ) Notice: Subject to any disclaimer, the term of this patent is extended or adjusted under 35 U.S.C. 154(b) by 0 days.

(21) Appl. No.: 13/111,324

(22) Filed: May 19, 2011

(65) Prior Publication Data

US 2011/0222065 A1 Sep. 15, 2011

Related U.S. Application Data

(62) Division of application No. 12/290,868, filed on Nov. 4, 2008, now Pat. No. 7,973,935.

(30) Foreign Application Priority Data

Nov. 6, 2007 (JP) ................................. 2007-288644
Nov. 6, 2007 (JP) ................................. 2007-288645

(51) Int. Cl.
*G01J 1/42* (2006.01)
*G01J 1/10* (2006.01)
*G01J 1/12* (2006.01)

(52) U.S. Cl. ......... 356/213; 356/228; 356/229; 356/230

(58) Field of Classification Search .......... 356/445–448, 356/450–458
See application file for complete search history.

(56) References Cited

U.S. PATENT DOCUMENTS

| | | | | |
|---|---|---|---|---|
| 4,284,356 A | * | 8/1981 | Heilman | 356/429 |
| 4,557,599 A | * | 12/1985 | Zimring | 356/243.1 |
| 5,252,836 A | * | 10/1993 | Matthews et al. | 250/559.18 |
| 6,198,527 B1 | * | 3/2001 | Nishi | 355/53 |

FOREIGN PATENT DOCUMENTS

| | | |
|---|---|---|
| JP | 2001-264173 | 9/2001 |
| JP | 2003-521700 | 7/2003 |

* cited by examiner

*Primary Examiner* — Gregory J Toatley
*Assistant Examiner* — Jarreas C Underwood
(74) *Attorney, Agent, or Firm* — Brinks Hofer Gilson & Lione

(57) ABSTRACT

A reflection characteristic measuring apparatus capable of scanning a specimen surface of a sheet specimen at a high speed is provided. The reflection characteristic measuring apparatus includes a group of illuminating and light-receiving systems for directing illuminating light onto the specimen surface of the sheet specimen held by a specimen holding roller pair and for receiving reflected light from the specimen surface. The illuminating and light-receiving systems measure a spectral characteristic of the received reflected light. The illuminating and light-receiving systems are disposed over one-dimensional arrays of color samples which extend in the longitudinal direction of the sheet specimen, and scan the one-dimensional arrays in a direction opposite to a direction in which the sheet specimen is transported.

4 Claims, 11 Drawing Sheets

TRANSPORT DIRECTION

TRANSPORT DIRECTION

F I G . 1 0
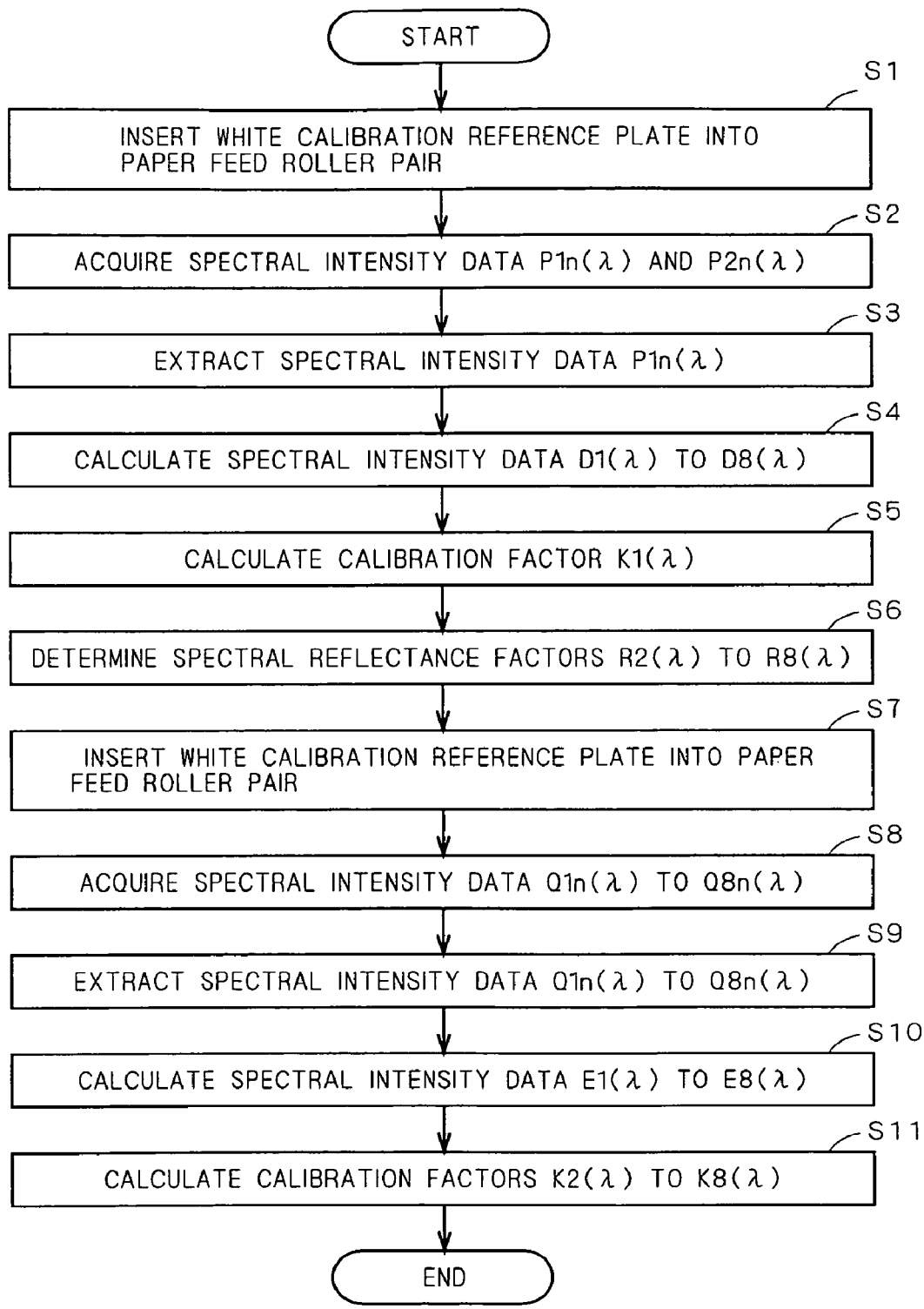

US 8,130,371 B2

METHOD OF CALIBRATING REFLECTION CHARACTERISTIC MEASURING APPARATUS FOR SHEET SPECIMEN

CROSS-REFERENCE TO RELATED APPLICATIONS

This is a divisional application of and claims the benefit of priority from application Ser. No. 12/290,868 filed Nov. 4, 2008, entitled "Reflection Characteristic Measuring Apparatus For Sheet Specimen, Method Of Calibrating Reflection Characteristic Measuring Apparatus For Sheet Specimen, And Calibration Reference Plate For Use In Calibration Of Reflection Characteristic Measuring Apparatus For Sheet Specimen."

This application is based on application Nos. 2007-288644 and 2007-288645 filed in Japan, the contents of which are hereby incorporated by reference.

BACKGROUND OF THE INVENTION

1. Field of the Invention

The present invention relates to a reflection characteristic measuring apparatus for a sheet specimen and, more particularly, to a reflection characteristic measuring apparatus which scans a sheet specimen on which a plurality of color samples for use in calibration of colors printed by printing devices are printed to continuously measure the reflection characteristics of the color samples arranged in a two-dimensional array. The present invention also relates to a method of calibrating the reflection characteristic measuring apparatus for a sheet specimen, and to a calibration reference plate for use in calibration of the reflection characteristic measuring apparatus for a sheet specimen.

2. Description of the Background Art

FIG. 13 is a schematic view showing an example of a sheet specimen 971 for use in calibration of colors printed by a printing device such as a color printer and the like. FIG. 13 is a plan view of the sheet specimen 971.

As shown in FIG. 13, the sheet specimen 971 has a specimen surface 972 on which a multiplicity of (typically, hundreds of) color samples 981 having different color tones and different densities are printed. The color samples 981 are typically rectangular or square in shape, and are arranged in a regular array both in the longitudinal direction and in the transverse direction of the sheet specimen 971. Such a sheet specimen 971 is also known as a "color patch chart" or the like.

For the calibration of a printing device, predetermined print data is initially inputted to the printing device to be calibrated to cause the printing device to print the color samples 981 shown in FIG. 13. Thereafter, the reflection characteristics of the printed color samples 981 are measured, and the colors printed by the printing device are calibrated based on differences between the measured values of the reflection characteristics and the reference values of the reflection characteristics which the color samples 981 should inherently have.

However, an attempt to measure the color samples 981 arranged in a two-dimensional array as shown in FIG. 13 by using a reflection characteristic measuring apparatus of a manual scan type as disclosed in National Publication of Translation No. 2003-521700 requires the manual scanning of the color samples 981 arranged in the two-dimensional array to result in complications.

To solve such a problem, a reflection characteristic measuring apparatus of an automatic scan type which automatically scans the color samples 981 arranged in a two-dimensional array has been put to practical use, as disclosed in Japanese Patent Application Laid-Open No. 2001-264173. The reflection characteristic measuring apparatus disclosed in Japanese Patent Application Laid-Open No. 2001-264173 measures a distance between an illuminating and light-receiving system and a specimen surface of a sheet specimen to correct the measured values of the reflection characteristics of the color samples 981, based on the measured value of the distance.

The reflection characteristic measuring apparatus disclosed in Japanese Patent Application Laid-Open No. 2001-264173, however, presents a problem in that it takes a long period of time to scan the color samples. The reflection characteristic measuring apparatus disclosed in Japanese Patent Application Laid-Open No. 2001-264173 presents another problem in necessitating a correction process to eliminate measurement errors resulting from variations in the distance between the illuminating and light-receiving system and the specimen surface of the sheet specimen.

SUMMARY OF THE INVENTION

The present invention is intended for a reflection characteristic measuring apparatus for a sheet specimen, a method of calibrating a reflection characteristic measuring apparatus for a sheet specimen, and a calibration reference plate for use in calibrating a reflection characteristic measuring apparatus for a sheet specimen.

According to a first aspect of the present invention, the reflection characteristic measuring apparatus for a sheet specimen comprises: a specimen holding part for holding a sheet specimen; a group of illuminating and light-receiving systems for directing illuminating light onto a specimen surface of the sheet specimen held by the specimen holding part and for receiving reflected light from the specimen surface of the sheet specimen to measure the received reflected light; and a scanning part for causing the sheet specimen held by the specimen holding part and the group of illuminating and light-receiving systems to move relative to each other, thereby causing the group of illuminating and light-receiving systems to scan the specimen surface of the sheet specimen, wherein the group of illuminating and light-receiving systems are discretely arranged in a direction nonparallel to a scanning direction in which the group of illuminating and light-receiving systems scan the specimen surface of the sheet specimen.

The reflection characteristic measuring apparatus is capable of scanning a plurality of one-dimensional arrays of color samples in parallel to measure a reflection characteristic of the color samples arranged in a two-dimensional array at a high speed.

A second aspect of the present invention is directed to a method of calibrating a group of illuminating and light-receiving systems provided in a reflection characteristic measuring apparatus for a sheet specimen, the group of illuminating and light-receiving systems directing illuminating light onto a specimen surface of the sheet specimen and receiving reflected light from the specimen surface of the sheet specimen to measure the received reflected light. The method comprises the steps of: (a) measuring a first reference area included in a calibration reference plate with a first illuminating and light-receiving system included among the group of illuminating and light-receiving systems; (b) measuring a second reference area other than the first reference area included in the calibration reference plate with the first illuminating and light-receiving system; (c) calibrating the first illuminating and light-receiving system, based on a result of measurement of the first reference area in the step (a); (d) applying a result of calibration in the step (c) to determine a reflection characteristic of the second reference area from a result of measurement of the second reference area in the step (b); (e) measuring the second reference area with a second illuminating and light-receiving system other than the first illuminating and light-receiving system included among the illuminating and light-receiving systems; and (f) calibrating the second illuminating and light-receiving system, based on the reflection characteristic determined in the step (d) and a result of measurement in the step (e).

The method is capable of reducing variations in calibration because the first illuminating and light-receiving system and the second illuminating and light-receiving system are calibrated in reference to the first reference area. Additionally, the method is capable of correctly calibrate the second illuminating and light-receiving system if the reflection characteristic of the second reference area is varied by changes with time. This permits other than the first reference area of the calibration reference plate to be made of a material which is prone to change in reflection characteristic with time.

A third aspect of the present invention is directed to a calibration reference plate for use in calibrating a group of illuminating and light-receiving systems provided in a reflection characteristic measuring apparatus for a sheet specimen, the group of illuminating and light-receiving systems directing illuminating light onto a specimen surface of the sheet specimen and receiving reflected light from the specimen surface of the sheet specimen to measure the received reflected light. The calibration reference plate comprises: a first reference area to be measured with a first illuminating and light-receiving system included among the group of illuminating and light-receiving systems, the first reference area having a previously assigned reflection characteristic; and a second reference area to be measured with the first illuminating and light-receiving system and a second illuminating and light-receiving system other than the first illuminating and light-receiving system included among the group of illuminating and light-receiving systems.

The calibration reference plate allows the reduction in variations in calibration because the first illuminating and light-receiving system and the second illuminating and light-receiving system are calibrated in reference to the first reference area. Additionally, the calibration reference plate allows the correct calibration of the second illuminating and light-receiving system if the reflection characteristic of the second reference area is varied by changes with time. This permits other than the first reference area of the calibration reference plate to be made of a material which is prone to change in reflection characteristic with time.

It is therefore a primary object of the present invention to measure a reflection characteristic of color samples arranged in a two-dimensional array at a high speed.

It is another object of the present invention to reduce variations in calibration to permit other than a first reference area of a calibration reference plate to be made of a material which is prone to change in reflection characteristic with time.

These and other objects, features, aspects and advantages of the present invention will become more apparent from the following detailed description of the present invention when taken in conjunction with the accompanying drawings.

BRIEF DESCRIPTION OF THE DRAWINGS

FIG. 10 is a flow diagram illustrating a procedure for white calibration;

DESCRIPTION OF THE PREFERRED EMBODIMENTS

<1 First Preferred Embodiment>
<1-1 Overview of Reflection Characteristic Measuring Apparatus 1>

Figure 1:
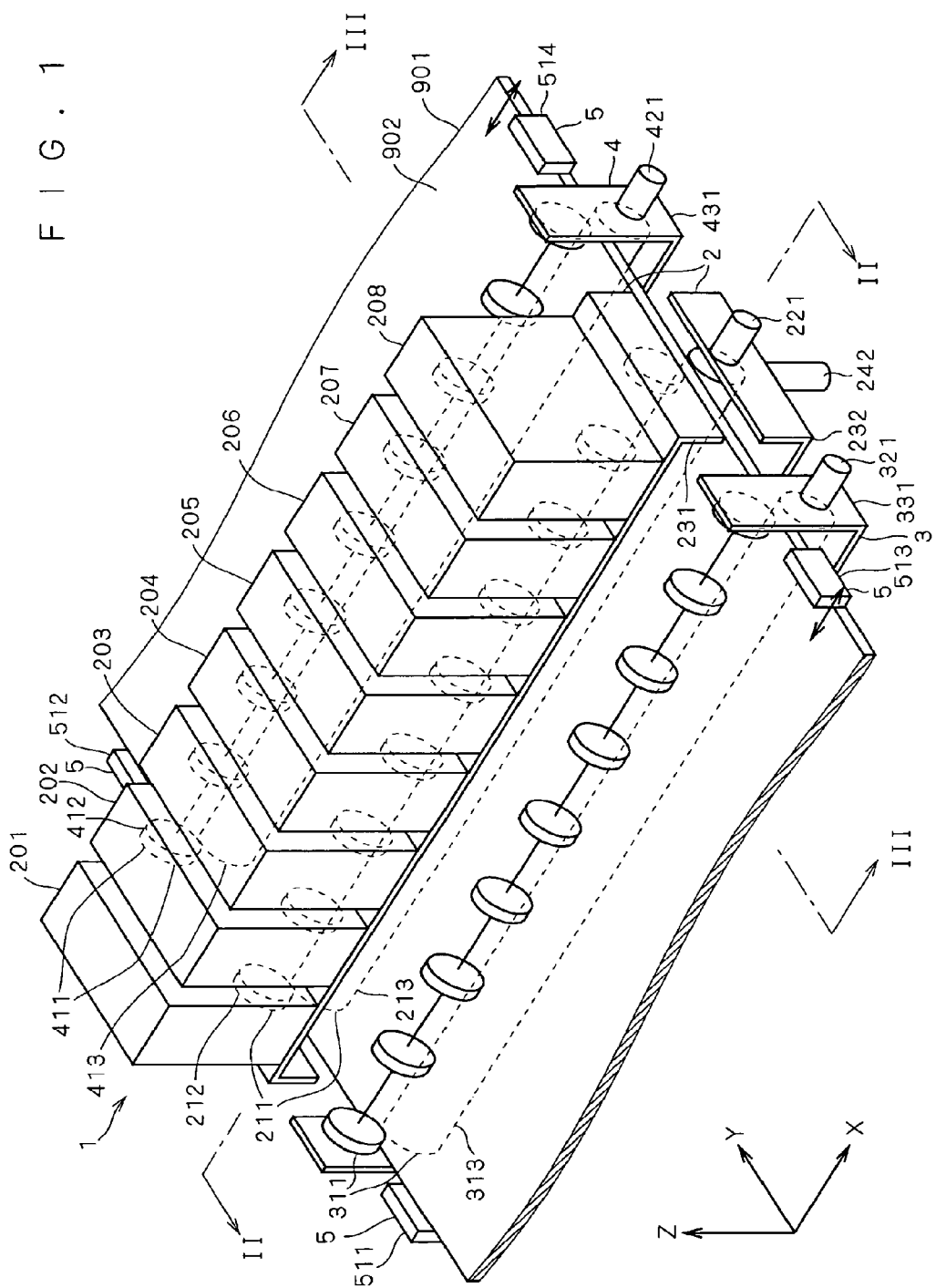
FIG. 1 is a perspective view of a reflection characteristic measuring apparatus according to a first preferred embodiment of the present invention.
Figure 2:
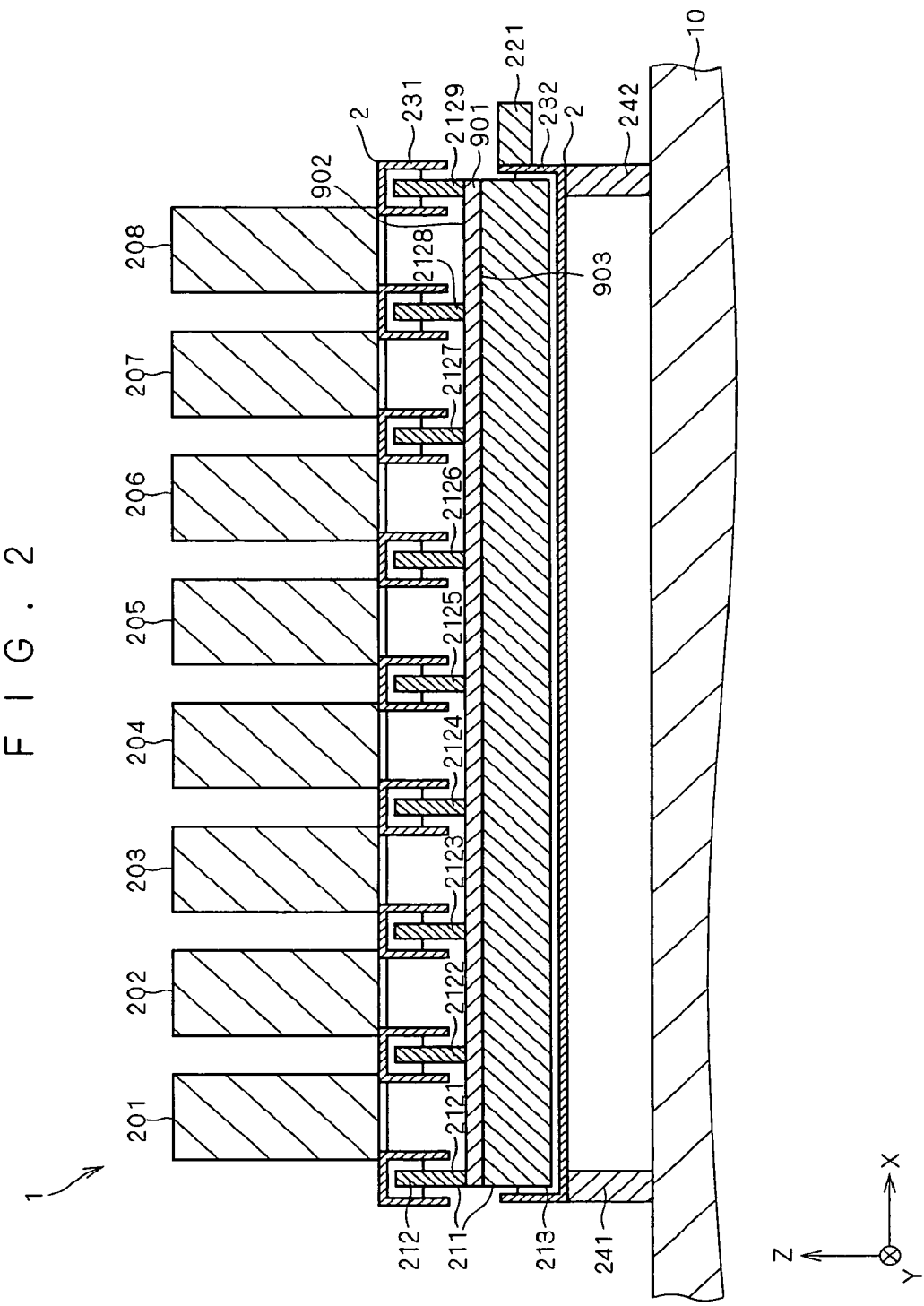
FIG. 2 is a sectional view of the reflection characteristic measuring apparatus taken along the line II-II of FIG. 1.
Figure 3:
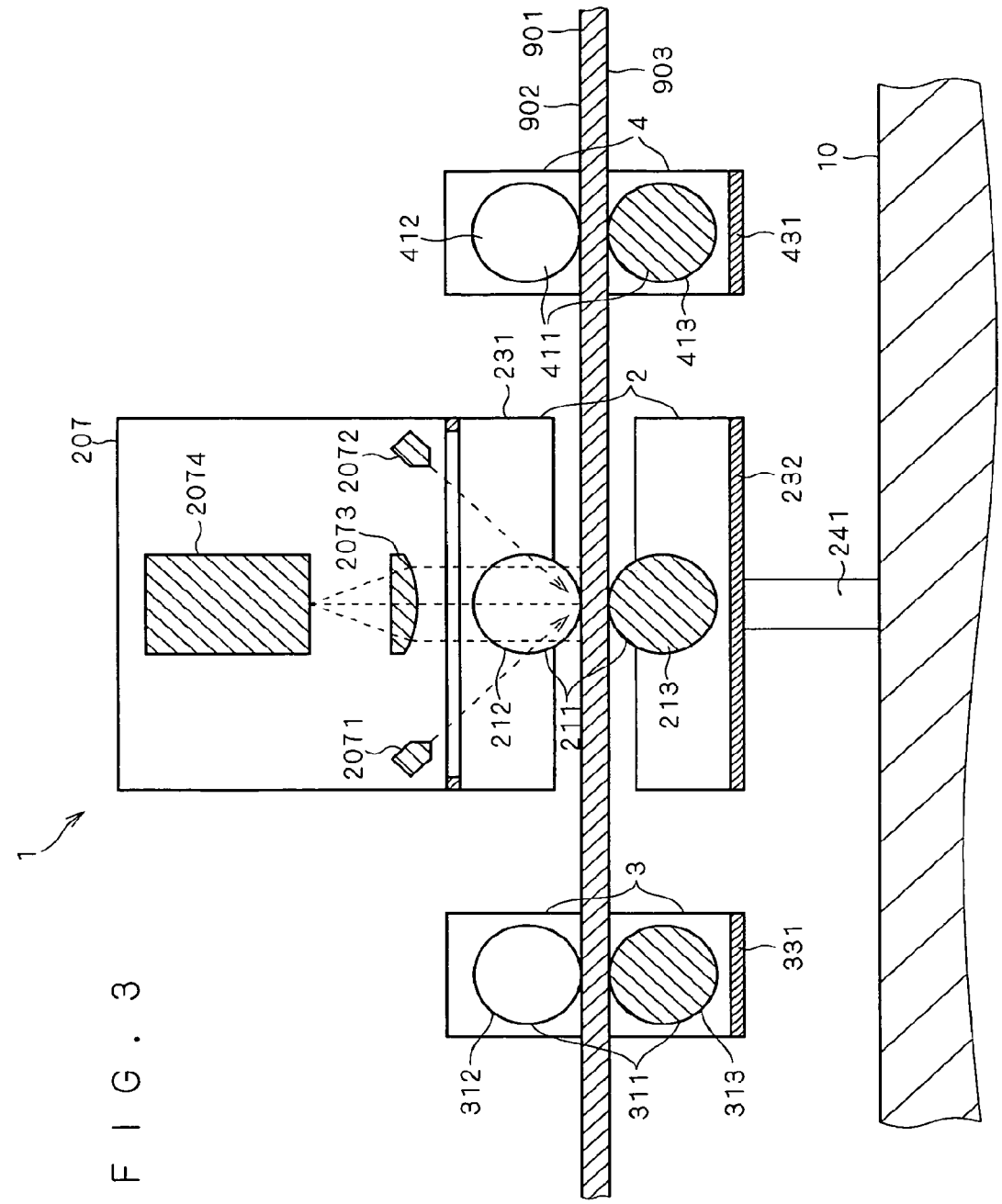
FIG. 3 is a sectional view of the reflection characteristic measuring apparatus taken along the line of FIG. 1.

FIGS. 1 to 3 are schematic views of principal parts of a reflection characteristic measuring apparatus 1 according to a first preferred embodiment of the present invention. FIG. 1 is a perspective view of the reflection characteristic measuring apparatus 1. FIG. 2 is a sectional view of the reflection characteristic measuring apparatus 1 taken along the line II-II of FIG. 1. FIG. 3 is a sectional view of the reflection characteristic measuring apparatus 1 taken along the line of FIG. 1. For convenience in illustration, FIGS. 1 to 3 include an XYZ rectangular coordinate system in which directions extending from front to rear, and vice versa, are defined as negative and positive X directions (±X directions), directions extending from right to left, and vice versa, are defined as negative and positive Y directions (±Y directions), and vertical directions extending from top to bottom, and vice versa, are defined as negative and positive Z directions (±Z directions). The reflection characteristic measuring apparatus 1 continuously measures the reflection characteristics of color samples 911 arranged in a two-dimensional array on a specimen surface 902 of a sheet specimen 901 shown in FIG. 5.

Figure 5:
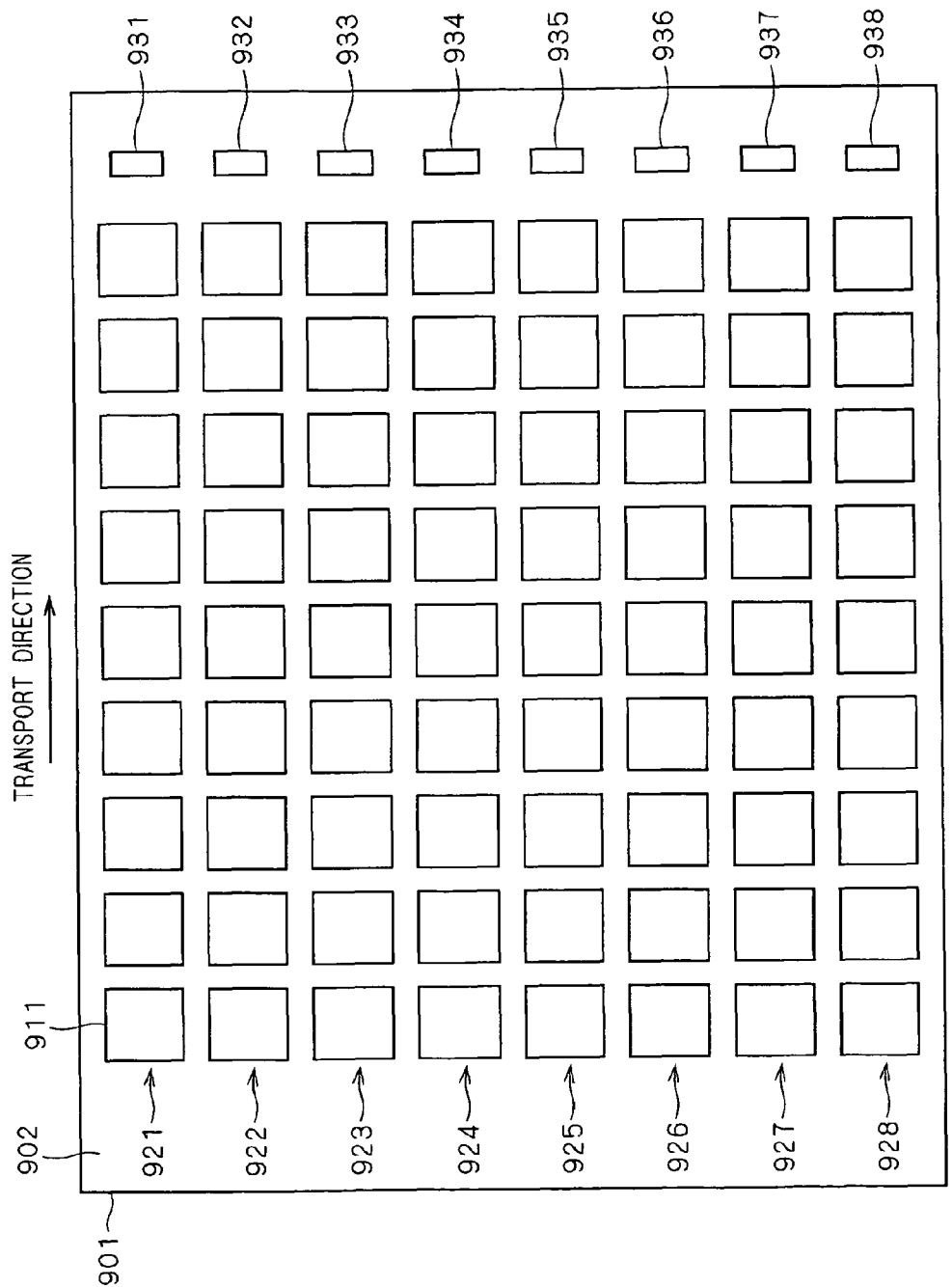
FIG. 5 is a plan view of a sheet specimen.

FIG. 5 is a schematic view showing an example of the sheet specimen 901 for use in the calibration of colors printed by a printing device such as a color printer and the like. FIG. 5 is a plan view of the sheet specimen 901. The sheet specimen 901 is in the form of a rectangular sheet. The multiplicity of (typically, hundreds of) color samples 911 having different color tones and different densities are printed to form a lattice on the specimen surface 902 of the sheet specimen 901. The color samples 911 are rectangular or square in shape, and are arranged in a regular array both in the longitudinal direction and in the transverse direction of the sheet specimen 901. The sheet specimen 901 is shown in FIG. 5 as having nine color samples 911 arranged in each row extending in the longitudinal direction, and eight color samples 911 arranged in each column extending in the transverse direction. However, the number of color samples 911 arranged in each row extending in the longitudinal direction and the number of color samples 911 arranged in each column extending in the transverse direction may be increased or decreased.

Referring again to FIGS. 1 to 3, the reflection characteristic measuring apparatus 1 principally includes a measuring part 2, a paper feed part 3, a paper output part 4, and a specimen guide 5. The reflection characteristic measuring apparatus 1 measures the reflection characteristics of the color samples 911 printed on the specimen surface 902 while transporting the sheet specimen 901 in the +Y direction. The sheet specimen 901 is transported in the longitudinal direction thereof, and the specimen surface 902 of the sheet specimen 901 being transported is parallel to an XY plane. While the sheet specimen 901 is being transported, the color samples 911 are arranged in a regular array both in the ±X directions and in the ±Y directions.

<1-2 Measuring Part 2>

The measuring part 2 holds and transports the sheet specimen 901 carried from the paper feed part 3 while applying tension to the sheet specimen 901, and measures the reflection characteristics of the color samples 911 printed on the specimen surface 902. The measuring part 2 includes illuminating and light-receiving systems 201 to 208, a specimen holding roller pair 211, a drive motor 221, frames 231 and 232, and springs 241 and 242.

{Illuminating and Light-Receiving Systems 201 to 208}

The illuminating and light-receiving systems 201 to 208 direct illuminating light onto the specimen surface 902 of the sheet specimen 901 held by the specimen holding roller pair 211, and receive reflected light from the specimen surface 902. The illuminating and light-receiving systems 201 to 208 also measure the spectral characteristics of the received reflected light.

Each of the illuminating and light-receiving systems 201 to 208 has the shape of a rectangular parallelepiped with a bottom surface serving as an illuminating and light-receiving surface for emitting illuminating light and for receiving reflected light. The illuminating and light-receiving systems 201 to 208 are fixed to the frame 231, with their illuminating and light-receiving surfaces facing toward a measurement area to be subjected to the measurement.

The illuminating and light-receiving systems 201 to 208 are arranged in a line in the ±X directions perpendicular to the transport direction of the sheet specimen 901 and parallel to the specimen surface 902. The illuminating and light-receiving systems 201 to 208 are equally spaced apart from each other, and the spacing therebetween is equal to the spacing at which the color samples 911 are arranged in the ±X directions.

The illuminating and light-receiving systems 201 to 208 are disposed over one-dimensional arrays 921 to 928, respectively, of the color samples 911 which extend in the longitudinal direction of the sheet specimen 901, and scan the one-dimensional arrays 921 to 928, respectively, in the −Y direction (referred to hereinafter as a "scanning direction") opposite to the transport direction. The discrete arrangement of the plurality of illuminating and light-receiving systems 201 to 208 in the ±X directions which are nonparallel to the scanning direction as described above allows the parallel scanning of the plurality of one-dimensional arrays 921 to 928 of the color samples 911, thereby accomplishing the high-speed measurement of the reflection characteristics of the color samples 911 arranged in the two-dimensional array. The term "nonparallel" used herein means that the plurality of illuminating and light-receiving systems 201 to 208 need not necessarily be arranged in a direction "perpendicular" to the scanning direction. Although the eight illuminating and light-receiving systems 201 to 208 are shown as disposed in FIGS. 1 to 3, the number of illuminating and light-receiving systems 201 to 208 is increased or decreased in accordance with the number of color samples 911 arranged in each column extending in the transverse direction of the sheet specimen 901.

As shown in FIG. 3, the illuminating and light-receiving system 207 includes white LEDs (Light Emitting Diodes) 2071 and 2072 which constitute an illuminating system for emitting the illuminating light, and an objective lens 2073 and a polychromator 2074 which constitute a light-receiving system for receiving the reflected light. The illuminating and light-receiving system 207 may include an optical element other than the objective lens 2073, for example a lens for directing the illuminating light from the white LEDs 2071 and 2072 to the measurement area, and the like. The illuminating system and the light-receiving system in the illuminating and light-receiving system 207 form what is called 45/0 geometry. Although only the internal structure of the illuminating and light-receiving system 207 is shown in FIG. 3, the internal structure of each of the illuminating and light-receiving systems 201 to 206, and 208 is similar to that of the illuminating and light-receiving system 207.

The two white LEDs 2071 and 2072 direct white illuminating light onto the specimen surface 902 at angles of ±45 degrees to the normal to the specimen surface 902. Other types of light sources capable of emitting light in the wavelength range of the reflection characteristics to be measured may be used in place of the white LEDs 2071 and 2072.

The objective lens 2073 directs the light reflected from the measurement area of the specimen surface 902 to the polychromator 2074. A direction in which the optical axis of the objective lens 2073 extends is the direction of the normal to the specimen surface 902.

The polychromator 2074 makes spectroscopic measurements of the light reflected from the measurement area of the specimen surface 902. The polychromator 2074 uses a concave diffraction grating to disperse a light beam according to its wavelength, and uses a sensor array to detect a planar image obtained by the dispersion. This enables the polychromator 2074 to at once measure spectral intensity data $D(\lambda)$ indicative of changes in intensity as a function of wavelength in the form of an output from the sensor array.

{Specimen Holding Roller Pair 211}

The specimen holding roller pair 211 includes a positioning roller 212 provided over a transport path and a pressure roller 213 provided under the transport path to nip the sheet specimen 901 therebetween, thereby holding the sheet specimen 901 in a position in which the reflection characteristics are to be measured. Further, the specimen holding roller pair 211 rotates the positioning roller 212 and the pressure roller 213 to thereby transport the sheet specimen 901 in the +Y direction while applying tension to the sheet specimen 901.

The positioning roller 212 includes an assembly of small rollers 2121 to 2129 having a generally disc-shaped configuration. The small rollers 2121 to 2129 are equally spaced apart from each other, and the spacing therebetween is equal to the spacing at which the illuminating and light-receiving systems 201 to 208 are arranged. The opposite ends of a rotary shaft of the small rollers 2121 to 2129 are held by bearings provided in the frame 231 so that the rotary shaft extends in the ±X directions perpendicular to the transport direction of the sheet specimen 901 and parallel to the specimen surface 902. The small rollers 2121 to 2129 are rotatable about the rotary shaft. The small rollers 2121 to 2129 come in contact with the specimen surface 902 of the sheet specimen 901 outside the measurement area. This prevents the positioning roller 212 from contacting the measurement area to reduce errors of measurement of the reflection characteristics.

The pressure roller 213 has a generally cylindrical configuration. The opposite ends of a rotary shaft of the pressure roller 213 are held by bearings provided in the frame 232 so that the rotary shaft extends in the ±X directions perpendicular to the transport direction of the sheet specimen 901 and parallel to the specimen surface 902. The pressure roller 213 is rotatable about the rotary shaft. The pressure roller 213 is opposed to the positioning roller 212, with the sheet specimen 901 therebetween, to contact a back surface 903 of the specimen surface 902, thereby pressing the back surface 903 of the sheet specimen 901 toward the positioning roller 212.

{Drive Motor 221 }

The drive motor 221 rotates the pressure roller 213. Thus, the drive motor 221 transports the sheet specimen 901 in contact with the pressure roller 213 in the +Y direction to cause the sheet specimen 901 and the illuminating and light-receiving systems 201 to 208 to move relative to each other in a direction parallel to the specimen surface 902, thereby causing the illuminating and light-receiving systems 201 to 208 to scan the specimen surface 902. Although only the drive motor 221 for rotating the pressure roller 213 is shown as provided in FIGS. 1 to 3, only a drive motor for rotating the positioning roller 212 may be provided in place of the drive motor 221 or the drive motor for rotating the positioning roller 212 may be provided together with the drive motor 221. In this manner, at least one of the pressure roller 213 and the positioning roller 212 is rotated to apply tension to the sheet specimen 901. This makes the sheet specimen 901 difficult to bend, thereby reducing errors of measurement of the reflection characteristics.

Typically, the drive motor 221 is an electromagnetic motor. It is desirable that an electromagnetic motor capable of easily controlling the angle of rotation and the speed of rotation such as a stepping motor and a servomotor be employed as the drive motor 221.

{Frame 231}

The frame 231 holds the illuminating and light-receiving systems 201 to 208 and the positioning roller 212. When the illuminating and light-receiving systems 201 to 208 and the positioning roller 212 are held by the same frame 231 in this manner, the position of an area of contact (or the area of nipping) in which the positioning roller 212 (the small rollers 2121 to 2129) contacts the specimen surface 902 relative to the illuminating and light-receiving systems 201 to 208 is held fixed independently of the thickness of the sheet specimen 901 and the like. Then, pressing the sheet specimen 901 toward the positioning roller 212 which is positioned brings the specimen surface 902 into contact with the positioning roller 212, thereby maintaining the distance between the illuminating and light-receiving systems 201 to 208 and the specimen surface 902 constant. This reduces errors of measurement of the reflection characteristics. The frame 231 is fixed to an enclosure of the reflection characteristic measuring apparatus 1, and is provided over the transport path. The frame 231 has sufficient rigidity to prevent the contact area in which the positioning roller 212 contacts the specimen surface 902 from being out of position relative to the illuminating and light-receiving systems 201 to 208 due to the deformation thereof. Of course, the positional relationship between the illuminating and light-receiving systems 201 to 208 and the positioning roller 212 relative to each other may be fixed by other means than fixing to the same frame 231. For example, the illuminating and light-receiving systems 201 to 208 and the positioning roller 212 may be formed integrally to fix the positional relationship between the illuminating and light-receiving systems 201 to 208 and the positioning roller 212 relative to each other.

{Frame 232}

The frame 232 holds the pressure roller 213 and the drive motor 221. The frame 232 is fixed to an enclosure 10 of the reflection characteristic measuring apparatus 1 with the springs 241 and 242, and is provided under the transport path.

{Springs 241 and 242}

The springs 241 and 242 urge the frame 232 toward the back surface 903. Of course, an elastic body other than the springs 241 and 242 may be used to urge the frame 232 or an actuator may be used to urge the frame 232. By urging the frame 232 in this manner, the pressure roller 213 held by the frame 232 can press the back surface 903 of the sheet specimen 901 toward the positioning roller 212.

<1-3 Paper Feed Part 3>

The paper feed part 3 feeds the supplied sheet specimen 901 to the measuring part 2. The paper feed part 3 includes a paper feed roller pair 311, a drive motor 321, and a frame 331.

{Paper Feed Roller Pair 311 }

The paper feed roller pair 311 includes a roller 312 provided over the transport path and a roller 313 provided under the transport path to nip the sheet specimen 901 therebetween, thereby transporting the sheet specimen 901 inserted in a gap between the rollers 312 and 313 in the +Y direction.

The roller 312 includes an assembly of small rollers having a generally disc-shaped configuration. The roller 313 has a generally cylindrical configuration. The opposite ends of a rotary shaft of each of the rollers 312 and 313 are held by bearings provided in the frame 331 so that the rotary shaft extends in the ±X directions perpendicular to the transport direction of the sheet specimen 901 and parallel to the specimen surface 902. The rollers 312 and 313 are rotatable about the respective rotary shafts.

{Drive Motor 321 }

The drive motor 321 rotates the roller 313 to transport the sheet specimen 901 in contact with the roller 313 in the +Y direction. As in the measuring part 2, of course, only a drive motor for rotating the roller 312 may be provided in place of the drive motor 321 or the drive motor for rotating the roller 312 may be provided together with the drive motor 321.

Typically, the drive motor 321 is also an electromagnetic motor. It is desirable that an electromagnetic motor capable of easily controlling the angle of rotation and the speed of rotation such as a stepping motor and a servomotor be employed as the drive motor 321.

{Frame 331 }

The frame 331 holds the rollers 312 and 313, and the drive motor 321.

<1-4 Paper Output Part 4>

The paper output part 4 ejects the sheet specimen 901 transported from the measuring part 2. The paper output part 4 includes a paper output roller pair 411, a drive motor 421, and a frame 431 which are similar to the corresponding components of the paper feed part 3.

<1-5 Specimen Guide 5>

The specimen guide 5 restricts the movement of the sheet specimen 901 lying in the transport path in the ±X directions perpendicular to the transport direction, and guides the sheet specimen 901 lying in the transport path in the +Y direction.

The specimen guide 5 includes fixed pieces 511 and 512 which abut against a first edge of the sheet specimen 901 lying in the transport path on the negative side of the X direction (or the left-hand edge of the sheet specimen 901 as viewed in FIGS. 1 and 2) to restrict the movement of the sheet specimen 901 lying in the transport path in the −X direction. The specimen guide 5 further includes movable pieces 513 and 514 which abut against a second edge of the sheet specimen 901 lying in the transport path on the positive side of the X direction (or the right-hand edge of the sheet specimen 901 as viewed in FIGS. 1 and 2) to restrict the movement of the sheet specimen 901 lying in the transport path in the +X direction. The movable pieces 513 and 514 are movable in the ±X directions. This allows the specimen guide 5 to guide the sheet specimen 901 of a variety of widths in the +Y direction.

<1-6 Control System>

Figure 4:
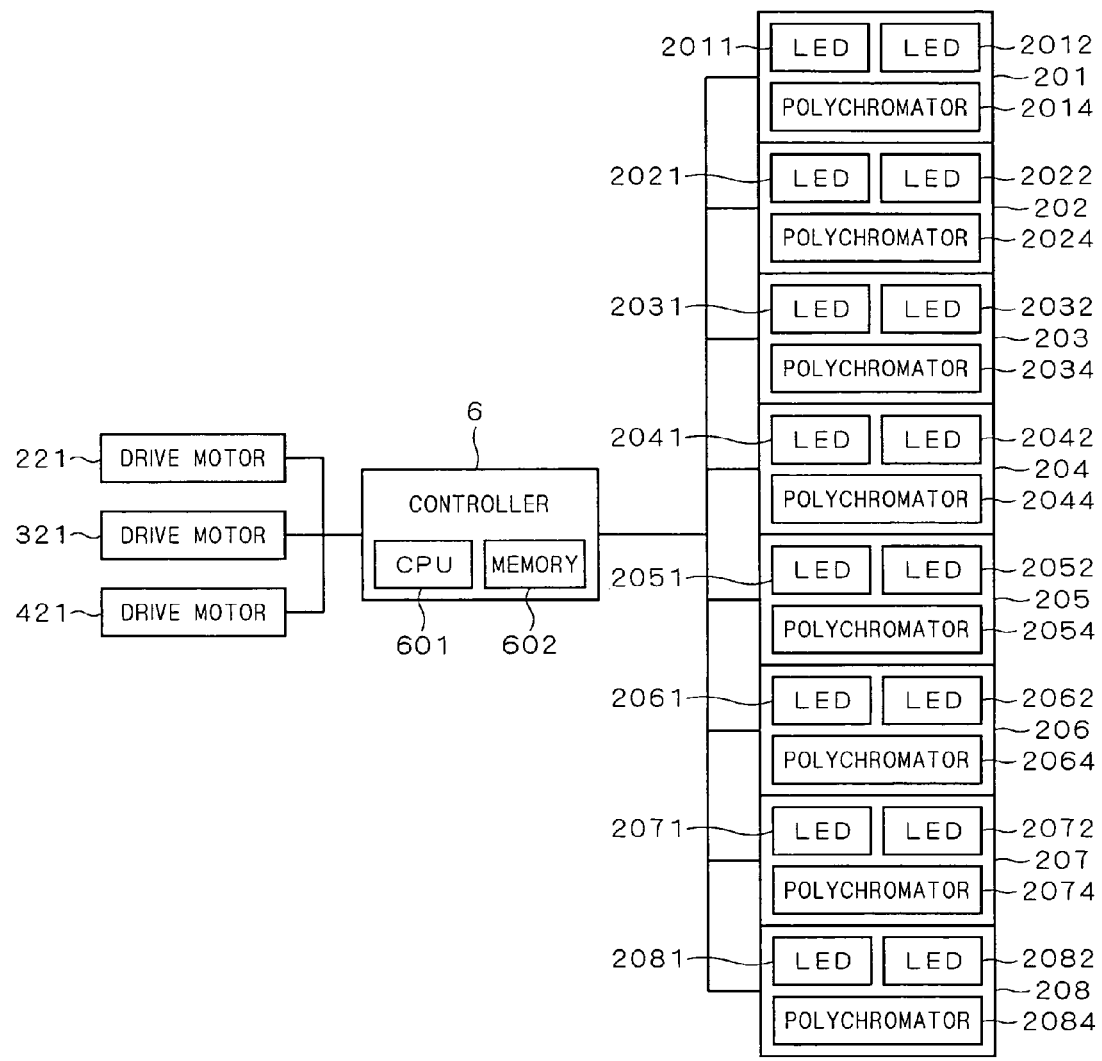
FIG. 4 is a block diagram illustrating a control system for the reflection characteristic measuring apparatus.

FIG. 4 is a block diagram illustrating a control system for the reflection characteristic measuring apparatus 1.

As shown in FIG. 4, the reflection characteristic measuring apparatus 1 includes a controller 6. The controller 6 controls the drive motors 221, 321 and 421, white LEDs 2011, 2012, 2021, 2022, 2031, 2032, 2041, 2042, 2051, 2052, 2061, 2062, 2071, 2072, 2081 and 2082 and polychromators 2014, 2024, 2034, 2044, 2054, 2064, 2074 and 2084 which are provided in the illuminating and light-receiving systems 201 to 208, and other constituents of the reflection characteristic measuring apparatus 1. The controller 6 also processes acquired data. The controller 6 is implemented by a built-in computer including at least a CPU 601 and a memory 602.

While supplying a driving signal to the drive motor 321 to cause the drive motor 321 to rotate the pressure roller 213, the controller 6 supplies power to the white LEDs 2011, 2012, 2021, 2022, 2031, 2032, 2041, 2042, 2051, 2052, 2061, 2062, 2071, 2072, 2081 and 2082 to turn on the white LEDs 2011, 2012, 2021, 2022, 2031, 2032, 2041, 2042, 2051, 2052, 2061, 2062, 2071, 2072, 2081 and 2082, and also controls the polychromators 2014, 2024, 2034, 2044, 2054, 2064, 2074 and 2084 to make spectroscopic measurements, thereby acquiring the spectral intensity data $D(\lambda)$ from the polychromators 2014, 2024, 2034, 2044, 2054, 2064, 2074 and 2084. Also, the controller 6 calculates a spectral reflectance factor $R(\lambda)$ which is a reflection characteristic of the sample from the acquired spectral intensity data $D(\lambda)$. The controller 6 may further calculate data about colors such as color values and the like from the spectral reflectance factor $R(\lambda)$. The result of measurements may be displayed on a display part provided in the reflection characteristic measuring apparatus 1 or be outputted to an external device such as a personal computer and the like.

Further, the controller 6 supplies relatively high power to the white LEDs 2011, 2012, 2021, 2022, 2031, 2032, 2041, 2042, 2051, 2052, 2061, 2062, 2071, 2072, 2081 and 2082 to provide a relatively high intensity of the illuminating light in an effective zone in which only a single color sample 911 is contained in the measurement area, and supplies relatively low power to the white LEDs 2011, 2012, 2021, 2022, 2031, 2032, 2041, 2042, 2051, 2052, 2061, 2062, 2071, 2072, 2081 and 2082 to provide a relatively low intensity of the illuminating light in an ineffective zone in which the measurement area extends over two color samples 911 so that the two color samples 911 are contained in the measurement area. This allows the illuminating light having an intensity sufficient to appropriately measure the reflection characteristics to impinge upon the measurement area in the effective zone in which it is possible to appropriately measure the reflection characteristics of the color samples 911, and allows the reduction in power consumption of the illuminating and light-receiving systems 201 to 208 in the ineffective zone in which it is impossible to appropriately measure the reflection characteristics.

A judgment as to whether the measurement area belongs to the effective zone or the ineffective zone is made, for example, based on the distance of transport of the sheet specimen 901, i.e. the angle of rotation of the drive motor 321, after the detection of reference marks 931 to 938 printed in the front of the respective one-dimensional arrays 921 to 928 of the color samples 911 on the specimen surface 902. The judgment as to whether the measurement area belongs to the effective zone or the ineffective zone may be made by other methods.

<1-7 White Calibration of Illuminating and Light-Receiving Systems 201 to 208>

{White Calibration Reference Plate 941}

Figure 6:
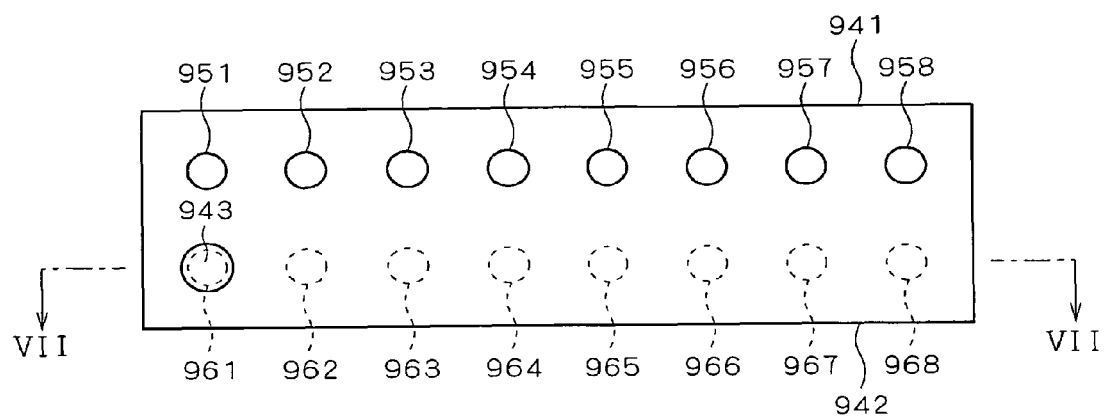
FIG. 6 is a plan view of a white calibration reference plate.
Figure 7:
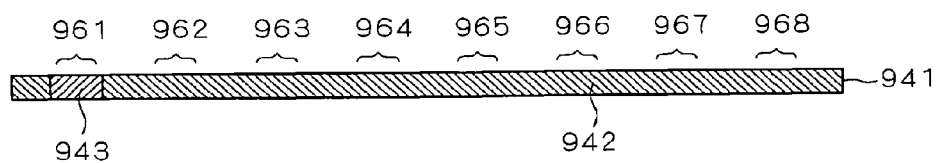
FIG. 7 is a sectional view of the white calibration reference plate.

FIGS. 6 and 7 are schematic views showing an example of a white calibration reference plate 941 for use in white calibration of the illuminating and light-receiving systems 201 to 208. FIG. 6 is a plan view of the white calibration reference plate 941. FIG. 7 is a sectional view of the white calibration reference plate 941 taken along the line VII-VII of FIG. 6.

As shown in FIGS. 6 and 7, the white calibration reference plate 941 is in the form of a rectangular plate. The white calibration reference plate 941 has a front surface formed with marks 951 to 958 for position detection. The marks 951 to 958 are circular in shape, and are arranged regularly in a line in the longitudinal direction of the white calibration reference plate 941. The spacing at which the marks 951 to 958 are arranged is equal to the spacing at which the illuminating and light-receiving systems 201 to 208 are arranged in the ±X directions. The positions spaced a distance L apart from the positions of the marks 951 to 958 in the transverse direction of the white calibration reference plate 941 serve as reference areas 961 to 968, respectively, based on which the white calibration is performed. Thus, the reference areas 961 to 968 included in the white calibration reference plate 941 are arranged regularly in a line in the longitudinal direction of the white calibration reference plate 941. The spacing at which the reference areas 961 to 968 are arranged is equal to the spacing at which the illuminating and light-receiving systems 201 to 208 are arranged in the ±X directions. Although the eight marks 951 to 958 and the eight reference areas 961 to 968 are shown in FIGS. 6 and 7, the number of marks and the number of reference areas are increased or decreased in accordance with the number of illuminating and light-receiving systems to be subjected to the white calibration. Although the marks 951 to 958 and the reference areas 961 to 968 are shown in FIGS. 6 and 7 as arranged in the longitudinal direction of the white calibration reference plate 941, the marks and the reference areas can be arranged in the transverse direction of the white calibration reference plate depending on the numbers of marks and reference areas, the spacings at which the marks and reference areas are arranged, the distance L and the like.

The white calibration reference plate 941 is configured such that a calibration reference disc 943 which is a white inorganic plate made of a hard material represented by artificial opal and ceramic is embedded in the position of the reference area 961 of a white plastic plate 942 which is a flexible material represented by tetrafluoroethylene. The surface of the white plastic plate 942 and the surface of the calibration reference disc 943 lie in the same plane.

Figure 8:
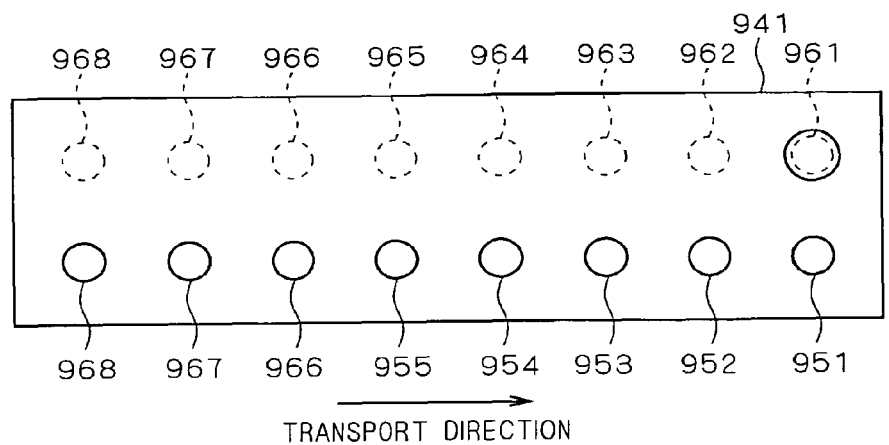
FIGS. 8 and 9 are views illustrating the transport directions of the white calibration reference plate.
Figure 9:
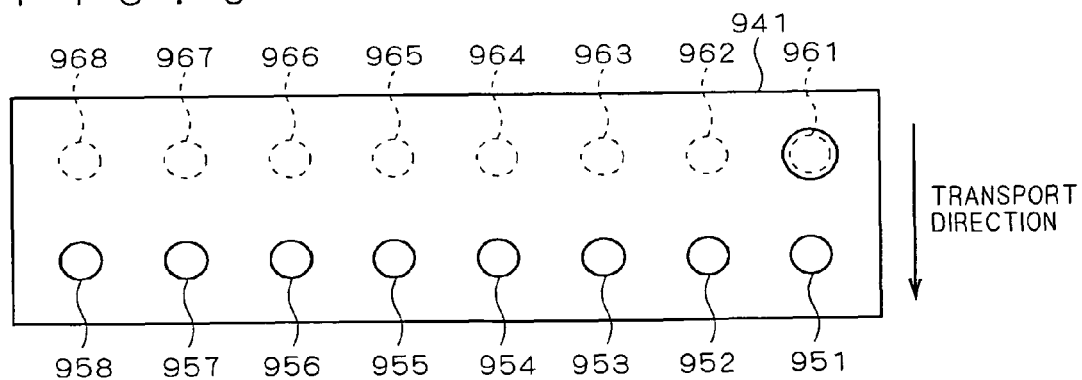

When such a white calibration reference plate 941 is inserted in the paper feed roller pair 311 so as to be transported in the longitudinal direction thereof as shown in FIG. 8, the reference areas 961 to 968 sequentially pass through the measurement area of the illuminating and light-receiving system 201, and the marks 951 to 958 sequentially pass through the measurement area of the illuminating and light-receiving system 202. On the other hand, when such a white calibration reference plate 941 is inserted in the paper feed roller pair 311 so as to be transported in the transverse direction thereof as shown in FIG. 9, the marks 951 to 958 pass through the measurement areas of the illuminating and light-receiving systems 201 to 208, respectively, and thereafter the reference areas 961 to 968 pass through the measurement areas of the illuminating and light-receiving systems 201 to 208, respectively. In this process, the reflection characteristic measuring apparatus 1 uses the mark 951 to identify the positions of the respective reference areas 961 to 968, thereby measuring the spectral intensity data D(λ) about the light reflected from the reference areas 961 to 968.

{Procedure for White Calibration}

FIG. 10 is a flow diagram illustrating a procedure for the white calibration.

For the white calibration, the distance between the fixed piece 511 and the movable piece 513 and the distance between the fixed piece 512 and the movable piece 514 are initially made equal to the width along the transverse direction of the white calibration reference plate 941, and the white calibration reference plate 941 is inserted into the paper feed roller pair 311 so as to be transported in the longitudinal direction thereof (in Step S1), as shown in FIG. 10. Then, the white calibration reference plate 941 is transported in the longitudinal direction thereof so that the reference areas 961 to 968 sequentially pass through the measurement area of the illuminating and light-receiving system 201, and the marks 951 to 958 sequentially pass through the measurement area of the illuminating and light-receiving system 202.

During this time, the controller 6 controls the illuminating and light-receiving systems 201 and 202 to acquire spectral intensity data P1n(λ) measured by the illuminating and light-receiving system 201 and spectral intensity data P2n(λ) measured by the illuminating and light-receiving system 202 repeatedly with a constant period (in Step S2). Subsequently, the controller 6 determines times $T_{11}$ to $T_{18}$ at which the marks 951 to 958 lie in the measurement area of the illuminating and light-receiving system 202 from the spectral intensity data P2n(λ) to extract the spectral intensity data P1n(λ) measured at the times $T_{11}$ to $T_{18}$ by the illuminating and light-receiving system 201 as spectral intensity data about the reference areas 961 to 968 (in Step S3). Subsequently, the controller 6 takes the average of the plurality of extracted spectral intensity data P1n(λ) for each of the reference areas 961 to 968 to calculate spectral intensity data D1(λ) to D8(λ) about the respective reference areas 961 to 968 (in Step S4).

After the illuminating and light-receiving system 201 measures the spectral intensity data D1(λ) to D8(λ) about the respective reference areas 961 to 968, the controller 6 calculates a calibration factor K1(λ) for the illuminating and light-receiving system 201 according to Equation (1), based on the result of measurement of the spectral intensity data D1(λ) about the reference area 961 in which the calibration reference disc 943 is embedded (in Step S5).

$$K1(\lambda) = \frac{R1(\lambda)}{D1(\lambda)} \quad (1)$$

where R1(λ) is a known spectral reflectance factor previously assigned for the reference area 961. The calibration reference disc 943 made of a hard material and embedded in the reference area 961 is suitable as a reference for the spectral reflectance factor because the calibration reference disc 943 has a scratch-resistant surface and exhibits small changes in spectral reflectance factor with time. Thus, the calibration factor K1(λ) calculated according to Equation (1) is used for the white calibration of the illuminating and light-receiving system 201. This allows the determination of the correct spectral reflectance factor R(λ) from the spectral intensity data D(λ) measured by the illuminating and light-receiving system 201.

Then, the controller 6 determines spectral reflectance factors R2(λ) to R8(λ) for the respective reference areas 962 to 968 from the results of measurement of the spectral intensity data D2(λ) to D8(λ) about the reference areas 962 to 968 in which the calibration reference disc 943 is not embedded according to Equation (2) (in Step S6). Thus, the illuminating and light-receiving system 201 subjected to the white calibration makes spectroscopic measurements of the reference areas 962 to 968, and the calibration factor K1(λ) indicative of the result of calibration of the illuminating and light-receiving system 201 is applied to determine the spectral reflectance factors R2(λ) to R8(λ) for the reference areas 962 to 968.

$$Ri(\lambda) = K1(\lambda) \times Di(\lambda) \ (i=2, 3, \ldots, 8) \quad (2)$$

The white plastic plate 942 made of a flexible material is not suitable as a reference for the spectral reflectance factor as it is because the white plastic plate 942 has a surface which is easily scratched and exhibits large changes in spectral reflectance factor with time. However, the calibration factor K1(λ) is applied to the result of measurement of the illuminating and light-receiving system 201 to correct the result of measurement of the illuminating and light-receiving system 201 in this manner. This allows the evaluation of the spectral reflectance factors R2(λ) to R8(λ) usable as a reference for the reference areas 962 to 968.

Next, the distance between the fixed piece 511 and the movable piece 513 and the distance between the fixed piece 512 and the movable piece 514 are made equal to the width along the longitudinal direction of the white calibration reference plate 941, and the white calibration reference plate 941 is inserted into the paper feed roller pair 311 so as to be transported in the transverse direction thereof (in Step S7). Then, the white calibration reference plate 941 is transported in the transverse direction thereof so that the reference areas 961 to 968 pass through the measurement areas of the illuminating and light-receiving systems 201 to 208, respectively, after the marks 951 to 958 pass through the measurement areas of the illuminating and light-receiving systems 201 to 208, respectively.

During this time, the controller 6 controls the illuminating and light-receiving systems 201 to 208 to acquire spectral intensity data Q1n(λ) to Q8n(λ) measured by the illuminating and light-receiving systems 201 to 208, respectively, repeatedly with a constant period (in Step S8). Subsequently, the controller 6 determines times $T_{21}$ to $T_{28}$ at which the marks 951 to 958 lie in the measurement areas of the illuminating and light-receiving systems 202 to 208 from the spectral intensity data Q1n(λ) to Q8n(λ) to extract the spectral intensity data Q1n(λ) to Q8n(λ) measured by the illuminating and light-receiving systems 201 to 208 at times $T_{31}$ to $T_{38}$ which are a time interval L/v later than the times $T_{21}$ to $T_{28}$ as spectral intensity data about the reference areas 961 to 968 (in Step S9) where v is the transport speed of the white calibration reference plate 941. Subsequently, the controller 6 takes the average of the plurality of extracted spectral intensity data for each of the reference areas 961 to 968 to calculate spectral intensity data E1(λ) to E8(λ) about the respective reference areas 961 to 968 (in Step S10).

After the illuminating and light-receiving systems 202 to 208 measure the spectral intensity data E2(λ) to E8(λ) about the respective reference areas 962 to 968, the controller 6 calculates calibration factors K2(λ) to K8(λ) for the illuminating and light-receiving systems 202 to 208 according to Equation (3) (in Step S11).

$$Ki(\lambda) = \frac{Ri(\lambda)}{Ei(\lambda)} \quad (i = 2, 3, \ldots, 8) \quad (3)$$

Spectral reflectance factors R1j(λ) to R8j(λ) for a j-th color sample in the one-dimensional arrays 921 to 928 are calculated from the calibration factor K1 determined in Step S5 and the calibration factors K2(λ) to K8(λ) determined in Step S11, based on the results of measurement of spectral intensity data E1j(λ) to E8j(λ) about the j-th color sample in the one-dimensional arrays 921 to 928. This calculation is given according to Equation (4). In other words, the illuminating and light-receiving systems 202 to 208 are calibrated, based on the spectral reflectance factors R2(λ) to R8(λ) for the reference areas 962 to 968 determined in Step S6 and the result of measurement of the spectral intensity data E2(λ) to E8(λ) about the reference areas 962 to 968.

$$Rij(\lambda) = Ki(\lambda) \times Eij(\lambda) \; (i=1, 2, \ldots, 8; \text{ and } j=1, 2, \ldots, 9) \quad (4)$$

According to this procedure for the white calibration, all of the illuminating and light-receiving systems 201 to 208 are calibrated with reference to the reference area 961. This reduces variations in calibration to reduce variations in measurement between the illuminating and light-receiving systems 201 to 208.

Also, according to this procedure for the white calibration, the illuminating and light-receiving systems 202 to 208 are correctly calibrated if the reflection characteristics of the reference areas 962 to 968 are varied by changes with time. This permits other than the reference area 961 of the white calibration reference plate 941 to be made of a material which is prone to change in reflection characteristics with time. Thus, the hybrid white calibration reference plate 941 comprised of a flexible material and a hard material may be employed, and the white calibration reference plate 941 which is easy to transport is produced at low costs.

This procedure for the white calibration produces the two above-mentioned effects not only when the illuminating and light-receiving systems 201 to 208 are discretely arranged in a direction nonparallel to the scanning direction but also when it is necessary for a reflection characteristic measuring apparatus including a plurality of illuminating and light-receiving systems to calibrate each of the plurality of illuminating and light-receiving systems.

Additionally, according to this procedure for the white calibration, the white calibration of the illuminating and light-receiving systems 201 to 208 is completed by only two scanning processes of the white calibration reference plate 941 transported in different directions. This makes the white calibration easy and convenient.

It is not necessary to perform both a first calibration sub-procedure composed of Steps S1 to S6 and a second calibration sub-procedure composed of Steps S7 to S11 each time the white calibration is performed. Both of the first and second calibration sub-procedures may be performed to store the spectral reflectance factors R1(λ) to R8(λ) when the white calibration is performed for the first time, and only the second calibration sub-procedure may be performed by using the stored spectral reflectance factors R2(λ) to R8(λ) when the white calibration is performed for the second and subsequent times.

<2. Second Preferred Embodiment>

Figure 11:
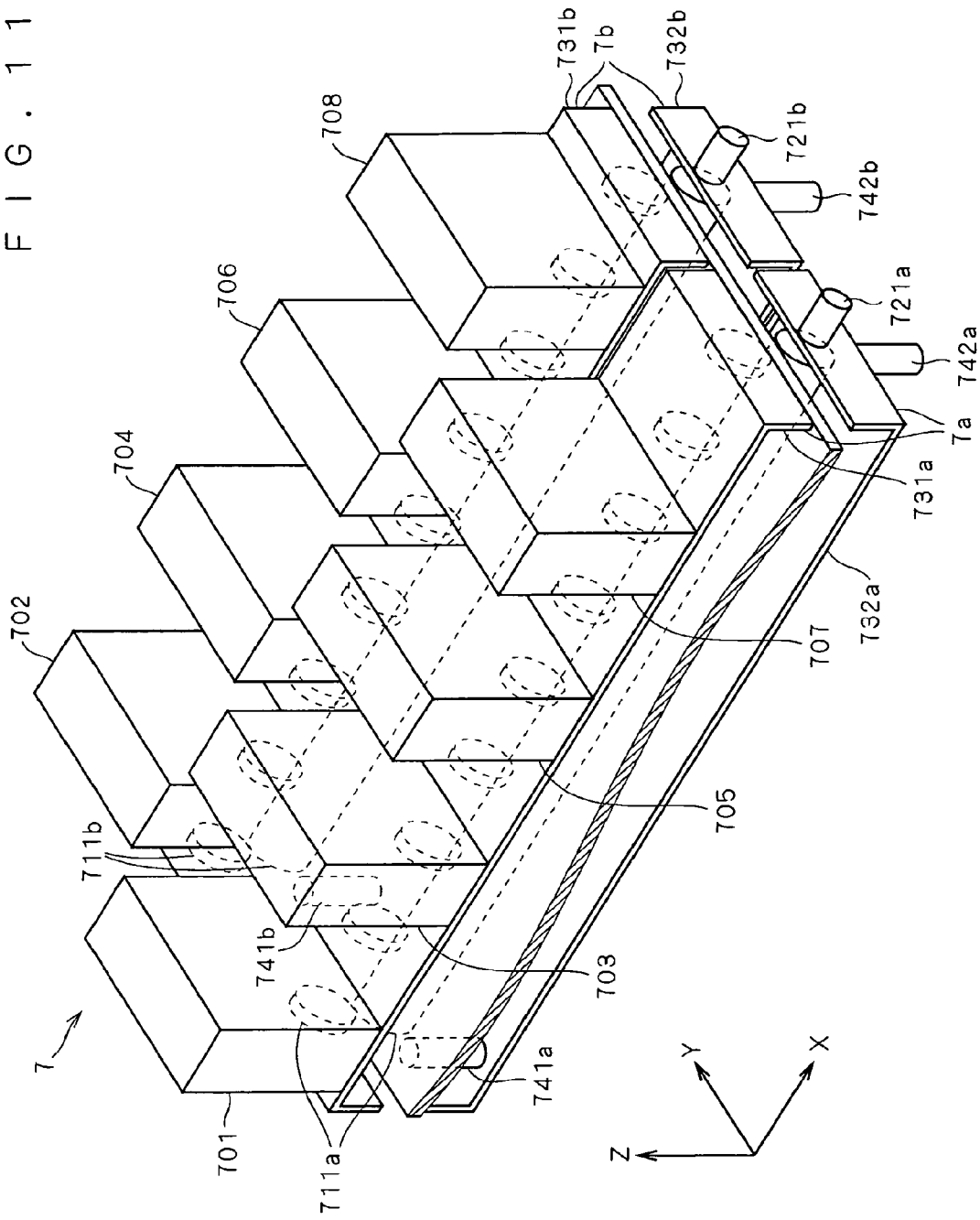
FIG. 11 is a perspective view of a measuring part according to a second preferred embodiment of the present invention.

FIG. 11 is a schematic view of principal parts of a measuring part 7 according to a second preferred embodiment of the present invention which is usable in place of the measuring part 2 of the reflection characteristic measuring apparatus 1 according to the first preferred embodiment. FIG. 11 is a perspective view of the measuring part 7. For convenience in illustration, FIG. 11 includes an XYZ rectangular coordinate system in which directions extending from front to rear, and vice versa, are defined as negative and positive X directions (±X directions), directions extending from right to left, and vice versa, are defined as negative and positive Y directions (±Y directions), and vertical directions extending from top to bottom, and vice versa, are defined as negative and positive Z directions (±Z directions).

The measuring part 7 includes a first measuring section 7a and a second measuring section 7b. The first measuring section 7a is provided upstream relative to the transport direction, and the second measuring section 7b is provided downstream relative to the transport direction.

The first measuring section 7a includes illuminating and light-receiving systems 701, 703, 705 and 707, a specimen holding roller pair 711a, a drive motor 721a, frames 731a and 732a, and springs 741a and 742a. The second measuring section 7b includes illuminating and light-receiving systems 702, 704, 706 and 708, a specimen holding roller pair 711b, a drive motor 721b, frames 731b and 732b, and springs 741b and 742b.

The illuminating and light-receiving systems 701 to 708 are similar to the illuminating and light-receiving systems 201 to 208 in the measuring part 2. Each of the illuminating and light-receiving systems 701 to 708 has the shape of a rectangular parallelepiped with a surface serving as an illuminating and light-receiving surface for emitting illuminating light and for receiving reflected light. The illuminating and light-receiving systems 701, 703, 705 and 707 are fixed to the frame 731a, with their illuminating and light-receiving surfaces facing toward a measurement area, and the illuminating and light-receiving systems 702, 704, 706 and 708 are fixed to the frame 731b, with their illuminating and light-receiving surfaces facing toward a measurement area.

The four illuminating and light-receiving systems 701, 703, 705 and 707 are arranged in a line in the ±X directions perpendicular to the transport direction and parallel to the specimen surface 902. The illuminating and light-receiving systems 701, 703, 705 and 707 are equally spaced apart from each other, and the spacing therebetween is equal to twice the spacing at which the color samples 911 are arranged in the ±X directions. Thus, the illuminating and light-receiving systems 701, 703, 705 and 707 are disposed over the one-dimensional arrays 921, 923, 925 and 927, respectively, of the color samples 911 which extend in the transport direction, and are capable of scanning the one-dimensional arrays 921, 923, 925 and 927 of the color samples 911 on the specimen surface 902 in the scanning direction opposite to the transport direction.

The four illuminating and light-receiving systems 702, 704, 706 and 708, on the other hand, are arranged in a line in the ±X directions perpendicular to the transport direction and parallel to the specimen surface 902. The illuminating and light-receiving systems 702, 704, 706 and 708 are equally spaced apart from each other, and the spacing therebetween is equal to twice the spacing at which the color samples 911 are arranged in the ±X directions. Thus, the illuminating and light-receiving systems 702, 704, 706 and 708 are disposed over the one-dimensional arrays 922, 924, 926 and 928, respectively, of the color samples 911 which extend in the transport direction, and are capable of scanning the one-dimensional arrays 922, 924, 926 and 928 of the color samples 911 on the specimen surface 902 in the scanning direction opposite to the transport direction.

The arrangement of the eight illuminating and light-receiving systems 701 to 708 in two lines, rather than in one line, achieves the discrete arrangement of the illuminating and light-receiving systems 701 to 708 not only in a direction nonparallel to the scanning direction but also in a direction parallel to the scanning direction. Such an arrangement allows the measurement areas of the illuminating and light-receiving systems 701 to 708 to belong to the effective zone at different times. As a result, this achieves the increase in power supplied to the LEDs of the illuminating and light-receiving systems 701 to 708 at different times to suppress the peak of power consumption of the reflection characteristic measuring apparatus, thereby reducing power supply burdens and costs. Additionally, when a spacing between the illuminating and light-receiving systems 701, 703, 705 and 707 and the illuminating and light-receiving systems 702, 704, 706 and 708 in the scanning direction is {n+(1/2)} times the spacing at which the color samples 911 are arranged in the scanning direction, the peak current consumption of the reflection characteristic measuring apparatus is especially reduced.

Further, when the illuminating and light-receiving systems 701 to 708 are discretely arranged in the scanning direction, the spacing at which the illuminating and light-receiving systems 701 to 708 are arranged in the ±X directions is twice the spacing at which the color samples 911 are arranged in the ±X directions. This provides room for installation space of the illuminating and light-receiving systems 701 to 708 to eliminate the need to unreasonably reduce the size of the illuminating and light-receiving systems 701 to 708. Conversely, when the size of the illuminating and light-receiving systems 701 to 708 remains the same, the spacing at which the color samples 911 are arranged may be decreased so that a greater number of color samples 911 are printed on the sheet specimen 901.

The illuminating and light-receiving systems 701 to 708 may be discretely arranged in three or more lines, rather than in two lines.

The specimen holding roller pair 711a, the drive motor 721a, the frames 731a and 732a, and the springs 741a and 742a of the first measuring section 7a are similar in function to the specimen holding roller pair 211, the drive motor 221, the frames 231 and 232, and the springs 241 and 242, respectively, of the measuring part 2 according to the first preferred embodiment. Also in the first measuring section 7a, pressing the sheet specimen 901 toward a positioning roller 712a which is positioned brings the specimen surface 902 into contact with a nipping area of the roller surface of the positioning roller 712a, thereby maintaining the distance between the illuminating and light-receiving systems 701, 703, 705 and 707 and the specimen surface 902 constant. This reduces errors of measurement of the reflection characteristics.

Likewise, the specimen holding roller pair 711b, the drive motor 721b, the frames 731b and 732b, and the springs 741b and 742b of the second measuring section 7b are similar in function to the specimen holding roller pair 211, the drive motor 221, the frames 231 and 232, and the springs 241 and 242, respectively, of the measuring part 2 according to the first preferred embodiment. Also in the second measuring section 7b, pressing the sheet specimen 901 toward a positioning roller 712b which is positioned brings the specimen surface 902 into contact with a nipping area of the roller surface of the positioning roller 712b, thereby maintaining the distance between the illuminating and light-receiving systems 702, 704, 706 and 708 and the specimen surface 902 constant. This reduces errors of measurement of the reflection characteristics.

<3. Modifications>

The reflection characteristic measuring apparatus 1 is configured to transport the sheet specimen 901, with the illuminating and light-receiving systems 201 to 208 fixed, to cause the sheet specimen 901 and the illuminating and light-receiving systems 201 to 208 to move relative to each other, thereby causing the illuminating and light-receiving systems 201 to 208 to scan the specimen surface 902. Alternatively, the reflection characteristic measuring apparatus 1 may be configured to transport the illuminating and light-receiving systems 201 to 208, with the sheet specimen 901 fixed, to cause the sheet specimen 901 and the illuminating and light-receiving systems 201 to 208 to move relative to each other, thereby causing the illuminating and light-receiving systems 201 to 208 to scan the specimen surface 902. Transporting theسheet specimen 901, with the illuminating and light-receiving systems 201 to 208 fixed, is advantageous in eliminating the need to move the heavy-weight illuminating and light-receiving systems 201 to 208 for the scanning.

In the reflection characteristic measuring apparatus 1, an instance in which the illuminating and light-receiving systems 201 to 208 make spectroscopic measurements is given. The present invention, however, is applicable to an instance in which the illuminating and light-receiving systems 201 to 208 measure the reflection characteristics without dispersing the reflected light according to its wavelength and an instance in which the illuminating and light-receiving systems 201 to 208 measure the reflection characteristics when monochromatic light is used.

Figure 12:
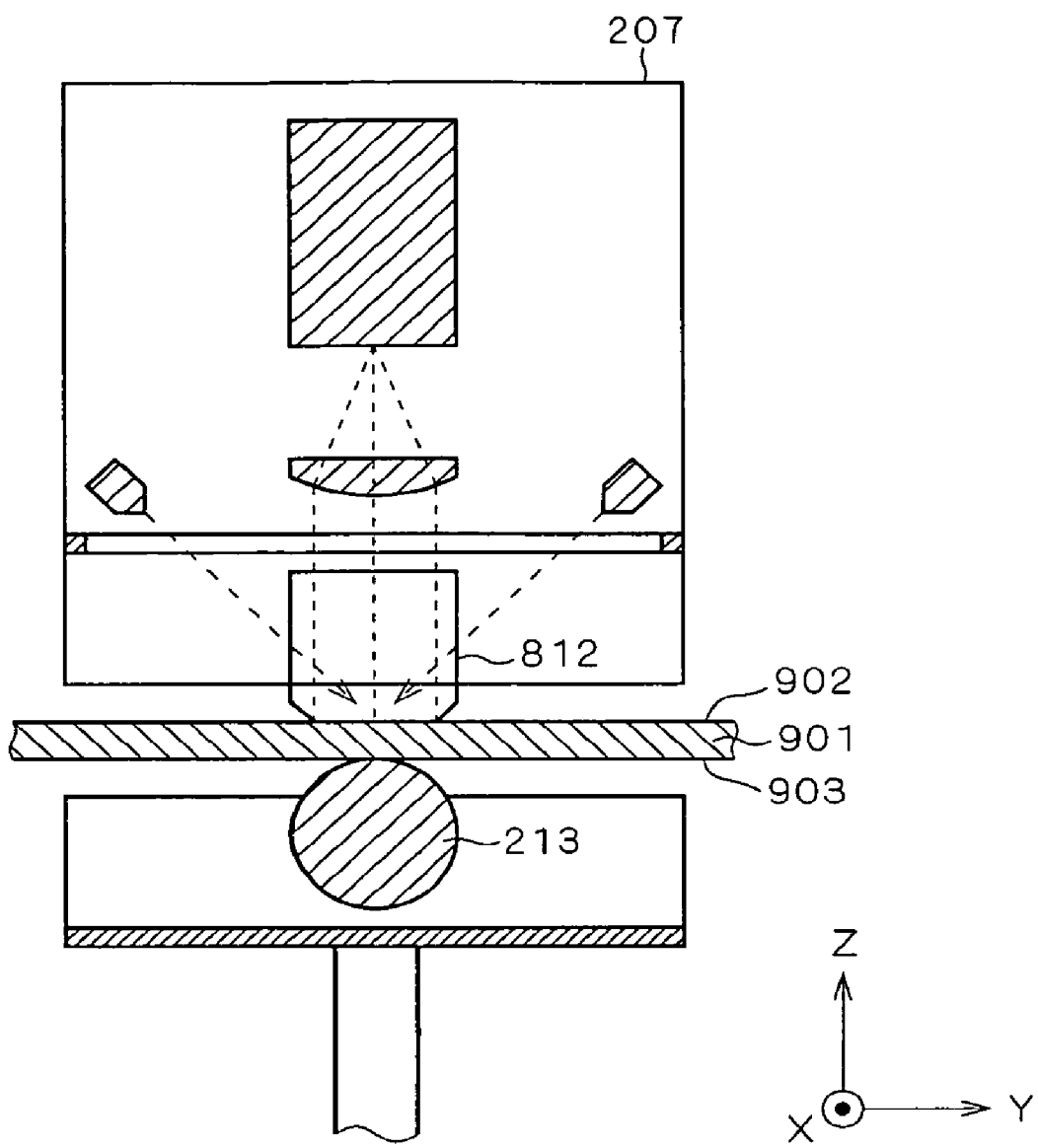
FIG. 12 is a sectional view illustrating a modification in which a contact member is provided in place of a positioning roller.
Figure 13:
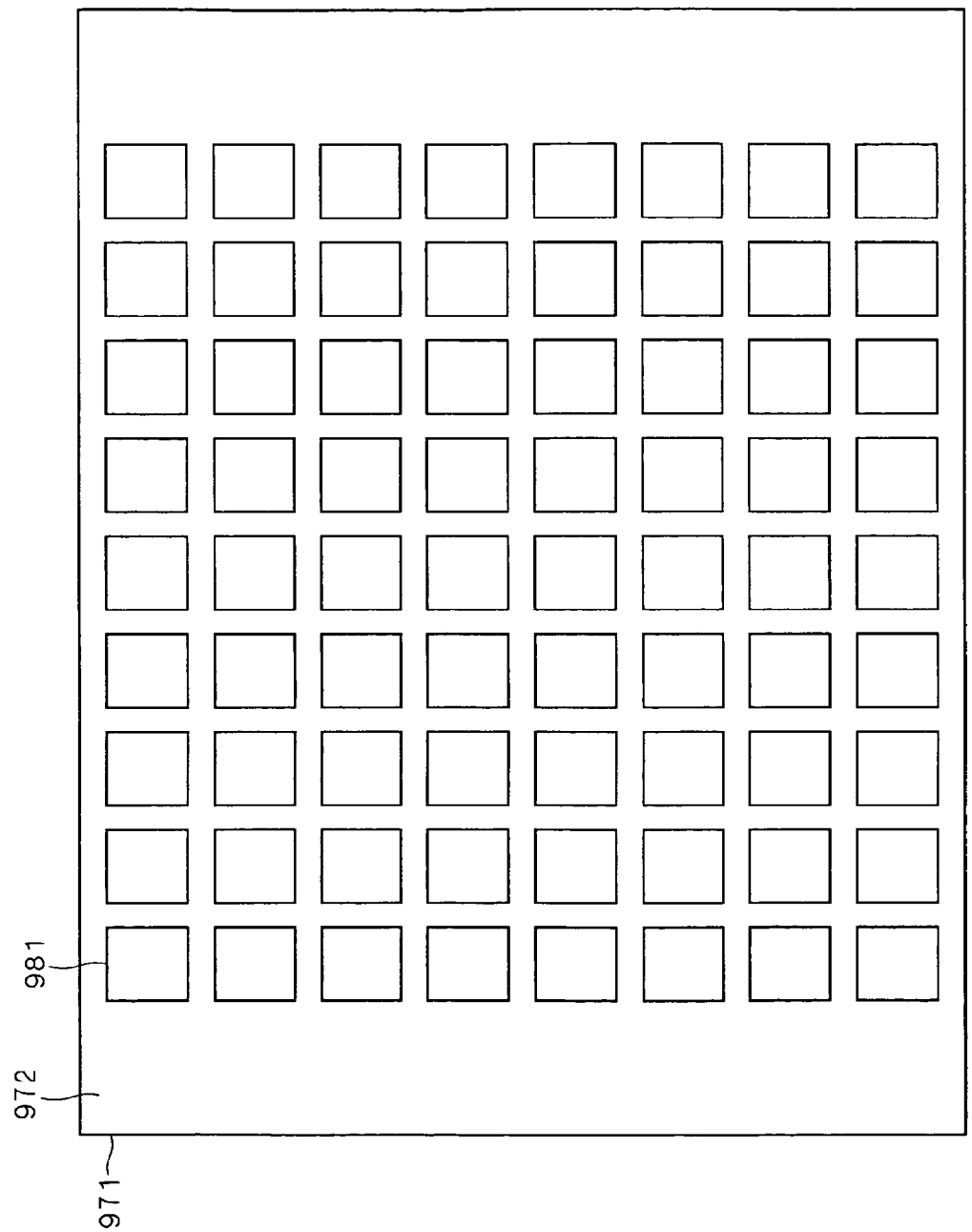
FIG. 13 is a plan view of a sheet specimen.

The method of maintaining the distance between the illuminating and light-receiving systems 201 to 208 and the specimen surface 902 constant is not limited to that described above. As an example, a contact member 812 having good slidability may be provided in place of the positioning roller 212, and the sheet specimen 901 be pressed against the fixed contact member 812, as shown in the sectional view of FIG. 12. A conceivable process for imparting good slidability to the contact member 812 is, for example, to form a film of fluororesin on the surface of the contact member 812.

While the invention has been described in detail, the foregoing description is in all aspects illustrative and not restrictive. It is understood that numerous other modifications and variations can be devised without departing from the scope of the invention.

What is claimed is:

1. A method of calibrating a group of illuminating and light-receiving systems provided in a reflection characteristic measuring apparatus for a sheet specimen, said group of illuminating and light-receiving systems directing illuminating light onto a specimen surface of the sheet specimen and receiving reflected light from the specimen surface of the sheet specimen to measure the received reflected light, said method comprising the steps of:

(a) measuring a first reference area included in a calibration reference plate with a first illuminating and light-receiving system included among said group of illuminating and light-receiving systems;

(b) measuring a second reference area other than the first reference area included in the calibration reference plate with said first illuminating and light-receiving system;

(c) calibrating said first illuminating and light-receiving system, based on a result of measurement of the first reference area in said step (a);

(d) applying a result of calibration in said step (c) to determine a reflection characteristic of the second reference area from a result of measurement of the second reference area in said step (b);

(e) measuring the second reference area with a second illuminating and light-receiving system other than said first illuminating and light-receiving system included among said illuminating and light-receiving systems;

(f) calibrating said second illuminating and light-receiving system, based on the reflection characteristic determined in said step (d) and a result of measurement in said step (e);

wherein the calibration reference plate in which the first reference area and the second reference area are arranged in a first direction, is used;

wherein steps (a) and (b) are executed by transporting the calibration reference plate in the first direction to cause the first reference area and the second reference area to pass through a measurement area of said first illuminating and light-receiving system; and wherein step (e) is executed by transporting the calibration reference plate in a second direction to cause the second reference area to pass through a measurement area of said second illuminating and light-receiving system.

2. A calibration reference plate for use in calibrating a group of illuminating and light-receiving systems provided in a reflection characteristic measuring apparatus for a sheet specimen, said group of illuminating and light-receiving systems directing illuminating light onto a specimen surface of the sheet specimen and receiving reflected light from the specimen surface of the sheet specimen to measure the received reflected light, said calibration reference plate comprising:

a first reference area to be measured with a first illuminating and light-receiving system included among said group of illuminating and light-receiving systems, said first reference area having a previously assigned reflection characteristic;

a second reference area to be measured with said first illuminating and light-receiving system and a second illuminating and light-receiving system other than said first illuminating and light-receiving system included among said group of illuminating and light-receiving systems;

a feed transport configured to transport the calibration reference plate in a first direction to cause the first reference area and the second reference area to pass through a measurement area of the first illuminating and light-receiving system; and the feed transport further configured to transport the calibration reference plate in a second direction to cause the second reference area to pass through a measurement area of the second illuminating and light-receiving system.

3. The calibration reference plate according to claim 2, wherein
said calibration reference plate being a white plastic plate with a white inorganic plate embedded in the position of the first reference area.

4. The calibration reference plate according to claim 2, further comprising
a position detecting mark spaced apart from the first reference area and the second reference area.

* * * * *